United States Patent [19]
Klatzmann et al.

[11] Patent Number: 6,140,114
[45] Date of Patent: Oct. 31, 2000

[54] DEFECTIVE VIRAL VACCINE PARTICLES OBTAINED IN VIVO OR EX VIVO

[75] Inventors: David Klatzmann; Jean-Loup Salzmann, both of Paris, France

[73] Assignee: Universite Pierre et Marie Curie (Paris VI), Paris, France

[21] Appl. No.: 09/166,147

[22] Filed: Oct. 5, 1998

[51] Int. Cl.$^7$ ...................................................... C12N 15/00
[52] U.S. Cl. .................................... 435/320.1; 424/184.1; 424/187.1; 424/188.1; 424/204.1; 435/FOR 147; 435/FOR 157; 435/FOR 180; 435/FOR 182; 435/FOR 190; 536/23.1; 536/23.72
[58] Field of Search ........................ 435/320.1, FOR 147, 435/FOR 148, FOR 157, FOR 180, FOR 182, FOR 190; 424/184.1, 185.1, 186.1, 187.1, 188.1, 189.1, 192.1, 196.11, 199.1, 204.1, 229.1; 935/22, 23, 32, 55, 57, 65; 536/23.1, 23.72

[56] References Cited

FOREIGN PATENT DOCUMENTS

| 0 611 822 | 8/1994 | European Pat. Off. |
|---|---|---|
| WO 91 02805 | 3/1991 | WIPO . |
| WO 93 17118 | 9/1993 | WIPO . |
| WO 93 20220 | 10/1993 | WIPO . |
| WO 94 29440 | 12/1994 | WIPO . |
| WO 96 26411 | 10/1995 | WIPO . |
| WO 96 05293 | 2/1996 | WIPO . |
| WO 96 06177 | 2/1996 | WIPO . |

OTHER PUBLICATIONS

Aids Research and Human Retroviruses, vol. 7, No. 12, Dec. 1991, pp. 991–998, XP000607853 Jenkins, S. et al.: "Formation of lentivirus particles by mammalian cells infected with recombinant fowlpox virus" see the whole document.

Virology, vol. 194, No. 1, May 1993, Orlando US, pp. 192–199, XP000608725 Dong, J. & Hunter E.: "Analysis of retroviral assembly using a Vaccinia/T7–polymerase complemenation system" see the whole document.

Gene Therapy, vol. 2, No. Suppl. 01, Nov. 17, 1995, p. S12XP000617926 Savard N Et Al.: "Transient Retroviral Packaging Systems Generated By Herpes Simplex Virus Derived Vectors" see abstract.

Vaccine, vol. 13, No. 11, Aug. 1995, pp. 1013–1022, XP000571592 Moldoveanu Z Et Al: "Immune Responses Induced By Administration Of Encapsidated Poliovirus Replicons Which Express HIV–1 GAG And Envelope Proteins" see the whole document.

Nature, vol. 379, No. 6562, Jan. 18, 1996, London GB, pp. 273–277, XP000608484 Diaz, J.J. et al.: "Post–transcriptional transactivation of human retroviral envelope glycoprotein expression by herpes simplex virus Us11 protein" cited in the application see the whole document.

Hasegawa et al. "Retroviral Transfer of HSV1–TK Gene into Human Lung Cancer Cell Line", *Journal of Molecular Medicine*, vol. 73, No. 73, (Mar. 1995), pp. 107–112. (complete reference).

*Primary Examiner*—Jeffrey Stucker
*Attorney, Agent, or Firm*—Nixon & Vanderhye p.c.

[57] ABSTRACT

The present invention relates to a vaccine consisting of defective viral particles as are obtained in vivo or ex vivo, in individuals infected or capable of being infected with a virus, after expression of the genes carried by a vector or a combination of vectors and comprising at least the structural genes necessary for the constitution of the viral particle.

24 Claims, 4 Drawing Sheets

🏁 ⓟ  promoteur diffèrent du LTR du virus considéré, type CMV, SV40, PGK, TK.....

|pA|  signal de polyadenylation diffèrent du LTR du virus considéré, type SV40, TK, HBV, .....

DEFECTIVE VIRAL VACCINE PARTICLES OBTAINED IN VIVO OR EX VIVO

The present invention relates to preventive or therapeutic vaccines consisting of viral particles as are obtained in vivo after the expression of genes carried by a plasmovirus.

A plasmovirus is defined as a plasmid or a viral vector carrying the set of sequences necessary for the reconstitution of a viral particle after expression in a host cell in vivo, in vitro or ex vivo. In other words, the introduction of the plasmovirus into the host cell transforms the latter into a virion-producing encapsidation cell.

Vaccination against viruses, and in particular retroviruses, is a complex operation. Some strategies have proved effective to a greater or lesser extent for vaccination against oncoviruses, but the trials on vaccines against lentiviruses do not give satisfactory results. One of the reasons which might explain this state of affairs is that the combination of phenomena leading to immunization against a virus probably requires the existence of physical viral particles and the production of these particles by cells of the host. A better proof thereof is that the best results of vaccination of monkeys against the SIV virus were obtained by the use of attenuated viruses which replicate in the vaccinated monkeys. A therapeutic vaccination strategy has been explored by Salk et al. (Proc. Natl. Acad. Sci. USA (1991) 88: 3348–52) using inactivated HIV particles. This strategy has proved unsatisfactory for two reasons. The first is that it is difficult to produce the HIV virus in vitro in sufficient quantity and the second is that the methods of inactivation of the said viruses, in order to be effective, destroyed part of the immunogenic epitopes of the viral particles.

The aim of the present invention is to cause the cell of the host to produce viral particles reproducing as closely as possible the wild-type viral particles but which are either attenuated or incapable of replicating in the host.

This vaccination approach consisting in injecting a plasmovirus, whose expression leads to the formation of viral particles, is particularly advantageous in the case where the vaccination by viral subunits has not yet been successful. The idea contained in this approach is that there is no better immunization than that obtained with a physical particle reproducing the infectious particle. It is in fact because of this that vaccination against numerous pathogenic agents and viruses in particular is carried out using these viruses in attenuated form. In particular, in the case of HIV infection, all the current trials show that the only way to effectively protect a macaque from SIV infection is the administration of an attenuated strain which effectively protects from a challenge against a different and pathogenic virus. Such an approach which is very questionable for the vaccination of man against HIV is confronted with the various problems of using an inactivated HIV which, through imperfect inactivation or through transcomplementations or mutations, could become virulent again. In the event of the construction of a plasmovirus made on an HIV structure, and lacking a number of genes except those allowing the physical particle to be reconstituted, the injection of such a plasmid should lead to the manufacture, by the cells, of all the proteins necessary for the manufacture of the viral particles lacking an infectious genome or, even better, empty. This approach may make it possible to produce in vivo not an attenuated, but a defective virus.

The inoculation of genes has been shown to be capable of generating an immune response after injection into mice (B. Wang et al. in Proc. Nat. Acad. Sci. USA 90: 4156, 1993) and Ulmer et al., Science, 1993, 259: 1745–1749) but the only response described therein is the production of antibodies.

The present invention relates to a new means of vaccination which, consisting of physical viral particles, either empty or containing a defective viral genome, attenuated or otherwise, and as obtained in vivo in human individuals or in animals infected or capable of being infected by a virus, after expression of a plasmovirus. The plasmovirus is a vector comprising the structural genes necessary for the constitution of the viral particle.

Attenuated viral genome is understood to mean any viral genome modified such that the replication is not very effective, for example a modification of a gene which would allow infection only through contact and not through dissemination, for example a deletion of the extracellular part of the env gene so as to retain only the fusogenic transmembrane part.

Any modification of the viral genome capable of conferring this attenuation characteristic on the virus may be defined by a test of infectivity in cell culture where, by conventional techniques, the level of infectious viruses present in the culture supernatant is considerably reduced whereas the infection from cell to cell is little affected by this modification.

The plasmovirus concept allowing reconstitution of viral particles may be used in various ways according to the properties which it is desired to confer on the final pharmaceutical product.

Various embodiments of the plasmovirus can be envisaged as long as on the same plasmid or vector, or on several associated plasmids or vectors, the set of sequences which, after having penetrated in the form of DNA or RNA into the cells and having become expressed therein, reconstitutes a physical viral particle.

Associated plasmids or vectors are understood to mean plasmids, vectors or nucleic acid sequences whose expression is substantially simultaneous in the cells and are either not linked or are directly or indirectly coupled, covalently or otherwise.

The embodiments are then chosen according to the function which it is desired to confer on the virion reconstituted from the plasmoviral construct.

By way of example, when the nucleocapsid structure of the virus is that of a retrovirus, it is sought to reproduce in the body a situation similar to that of the physiological infection by the virus in the sense that there is, on the one hand, a cell in the body producing the retroviral particles and therefore having, at its surface, antigens specific for the retrovirus and, on the other hand, there are released, into the medium outside this cell, retroviral particles which are exactly similar to those of the HIV virus, the only difference being that these particles are attenuated or incapable of replicating. The set of elements which make it possible to obtain an adequate immune response to the virus in question are therefore present simultaneously in the body.

The embodiments are varied and may favour either the safety, or efficiency, or selectivity towards a target, or the expression of a particular transgene, or several of these functions simultaneously.

The vector may in particular contain the gag gene or the gag and env genes or finally the gag, pol and env genes of the retrovirus, these genes being optionally under the control of independent and/or specific promoters, as well as transgenes of interest under the control of one or other promoter or of an independent promoter. A promoter is said to be specific or independent if it is different from the promoter of the virus which is reconstituted from the plasmovirus, for example from an LTR.

One embodiment of a vaccine according to the invention is that of a vaccine against a retrovirus, for example an HIV, and consisting in expressing by the cells of the host retroviral particles having the envelope proteins of the virus but lacking the viral genome.

In another embodiment, the cell of the host is transduced by a plasmovirus comprising the set of sequences necessary for the manufacture, by the cell, of a virus (gag, pol and env sequence and especially those of the HIV1 and/or HIV2 virus) but lacking the encapsidation sequence ψ, the pol gene comprising, where appropriate, mutations in INT and/or in RT, leading to the reconstitution, in the target cell, of an empty particle or of a particle carrying the defective genome.

In another embodiment, the host cell is transduced by a plasmovirus comprising the gag and pol sequences and having a mutated or deficient env gene.

Another embodiment is that where the plasmovirus has the encapsidation sequence but lacks certain genes, especially those for reverse transcriptase and/or for integrase, removing from the latter any capacity to replicate and/or to propagate in the body.

Nonlimiting examples of this type of constructs are illustrated in FIGS. 1 to 3.

It may be advantageous to insert a gene into the construct, and one whose expression is of interest either:
for the vaccinal treatment itself in order to increase the immunogenic response, for example by enhancing the onset of a cell and humoral type reaction simultaneously;
for increasing the safety of the system;
for allowing the development of an immune reaction against an epitope or an antigen for which the conventional systems provide disappointing results.

The gene may be inserted either under the control of the gag/pol promoters, or under the control of the env promoter. If its expression is under the control of a retrovirus LTR, and the nucleocapsid structure contains the ψ sequence, this gene will be reintegrated into the virions formed after transfection of the target cells, and its expression will be continued after the formation of the virion in situ.

Examples of genes whose expression is of interest associated with the vaccinal treatment, or linked to the safety of the system, are the following:

a) a gene encoding a conditional toxin, for example that of thymidine kinase or a functional equivalent: it is nowadays well known (see for example WO 95/22617) that the expression of this gene in dividing cells associated with a treatment with ganciclovir leads to the death of the cell containing it following incorporation of the nucleoside analogue into the DNA of the cells and subsequent stopping of replication. The advantage of the incorporation of this gene into the plasmovirus is to stop, where appropriate, a desired or accidental viral dissemination.

Any thymidine kinase derivative which preserves the phosphorylating function of the latter may be used; such is the case, for example, of the truncated derivatives as described in patent application No. PCT/FR/95/01098. More generally, any suicide gene, or even any gene whose product is capable of acting on the host cell or the virus under the action of a substance exogenous to the said virus, may be in the same manner integrated into the vector.

b) genes encoding immunomodulators. These may be for example:
cytokine genes: when the plasmovirus is injected by the intravenous route, a plasmovirus which would not have transfected cells and allowed the reconstitution of an infectious physical particle would then be captured by the reticuloendothelial system and the presence of genes encoding cytokines, in particular interleukins or G-CSF, GM-CSF;
or an MHC (major histocompatibility complex) protein should promote the antigenic presentation;
or a co-stimulation molecule such as B7-1 or B7-2 (Jenkins MK et al., 1993, Curr. Opin. immunol. 5: 361–367).

The product of such a locally secreted gene may also induce, as such, stimulation of the immune response.

c) genes or nucleotide sequences encoding peptides, polypeptides or proteins for which it is desired to trigger or increase immunogenicity: these may be, for example, haptens or the epitope of an antigen against which it is desired to develop immunization. The viral particle reconstituted from the plasmovirus in a way plays the role of an adjuvant or of a carrier conferring immunogenicity on the particular antigen or epitope. In the latter case, it is particularly advantageous to insert the complementary sequence into a region of the env gene which makes it possible to retain the functionality of the extra-membrane part of the envelope protein while having acquired the particular epitope structure expressed at the surface of the viral particle.

In all cases, it is the physical particle reconstituted in vivo which acts as a vaccine eliciting a cellular and humoral response. This approach is particularly advantageous in the case of the search for a vaccine protective against a virus for which it has not been possible to develop any vaccine. Such is the case especially for the HIVs and the HTLVs, type D retroviruses or spumaviruses, for which all attempts to develop vaccines have proved inadequate with respect to their protective effect (Medecine/Science, 1996 No. 1 volume 12, pages 87–93). Thus, in the present invention, the vaccine is particularly advantageous when the viral genome of the plasmovirus is that of a retrovirus, and the coding vector contains at least one HIV structural gene.

The properties of the plasmoviruses, and therefore of the vaccines of the invention, also result from the envelope type used. Indeed, the envelope protein is not only involved in the efficiency of production of infectious mature particles but also makes it possible to confer specificity of infection (tropism) on this particle because it is this protein which is involved in the phenomena of binding of the virion to the cell via the membrane receptors, and it is involved in the fusion of the viral and plasma membranes, which allows the release of the nucleocapsid into the cytoplasm of the infected cells. Finally, the envelope plays an important role in the resistance of the vector to inactivation by the complement. In this manner, on a nucleocapsid structure, it is possible to modify the spectrum of infection of the vector by modifying the gene for the envelope, thus making it possible to adapt it to the vaccine strategy which it is desired to adopt.

By way of example, it has been observed that vectors comprising the env gene of VSV (vesicular stomatitis virus) have a wide tropism towards the target cells, this ubiquitous type character resulting from the nature of the membrane receptor of this envelope. By contrast, env genes derived from ecotropic viruses will have a much narrower specificity.

A gene or a gene fragment encoding a peptide, a polypeptide or a protein may also be inserted into the N-terminal part of the env gene, as described by VALSESIA-WITTMANN et al., Journal, of Virology, (1996), pp 2059–2064, and this without interfering with the binding of the virion with its receptor on the target cells. During the reconstitution of the viral particle, the peptide or the polypeptide resulting from the translation of the gene or fragment inserted will be covalently combined with the N-terminal part of the viral envelope, that is to say in the extra-membrane part of the particle.

This property may be advantageously exploited to confer on the particle reconstituted from the plasmovirus various properties which may in particular be the following:

a) triggering of a cell-mediated immune reaction.

When the peptide, polypeptide or protein—all of which will be called "insert"—is expressed at the surface of the reconstituted viral molecule, this can lead to stimulation of cell-mediated immunity by activation of the T cells and simultaneously activation of the macrophages or of the antibody-producing B cells. This capacity can thus be exploited in order to increase the immunogenicity of the viral particle thus reconstituted. When the insert is a vaccinating antigen, the particle reconstituted from the plasmovirus may then be an adjuvant which increases, as such, the immune response to the antigen expressed at the surface of the particle.

b) triggering of an immune response towards a hapten:

A hapten is an antigenic determinant lacking, by itself, immunogenic power. An antigenic reaction against haptens is triggered and/or amplified by coupling the hapten to a carrier which may be, for example, albumin, PPD (purified protein derivatives of tuberculin) or KLH. Generally, the carrier is recognized by the T lymphocytes, whereas the hapten interacts with the B-type cells. The polypeptide haptens are then good candidates as "inserts".

c) routing function:

When the "insert" is chosen for its affinity towards a receptor specific for a target cell, whether the latter is inserted into or isolated from an organ, the viral particle expressing this "insert" may then be directed preferably at the given target so as to specifically trigger its action therein. If the action is simply the triggering of a cellular or humoral immunity reaction, the routing may take place directly on the T cells. If, on the other hand, a transgene is inserted into the plasmid, as is represented for example in FIG. 2, the routing makes it possible to target specifically the gene in question in the cell in which it has to be expressed in order to obtain optimum immunogenicity as long as the viral particle has properties of infectivity towards this target cell.

d) the three properties described above are of course not mutually exclusive and may be complementary so as to make therefrom vaccinating particles having increased immunogenicity and/or specificity.

In the same manner, it has been shown that a type 1 herpes simplex virus (HSV-1) protein called Us11 is capable of activating in trans the expression of the envelope glycoprotein of the retrovirus and especially of HIV or of HTLV (J. Diaz et al. (1996), Nature 379: 273). The inclusion of the gene encoding Us11 into the plasmovirus, either under the control of the retrovirus promoter, or under the control of another promoter, for example the pCMV promoter used for the transcription of a structural gene of the retrovirus, is particularly advantageous.

Accordingly, and according to the gene or the gene fragment which it is desired to express, it will be possible to determine the target cells which it is desired to target, the env gene and the site of insertion.

A first example of plasmovirus construct is represented in FIG. 1. It comprises:

a) the gag and pol genes under the control of a specific promoter;

b) an env gene also under the control of a specific promoter;

c) a polyadenylation signal different from the LTR of the virus in question, of the SV40, TK or HBV type and the like, d) where appropriate, the $\psi$ sequence, e) where appropriate, a gene or gene fragment of interest whose expression depends either on the promoter in a) or the promoter in b) or on an independent expression cassette.

In this construct, any reconstitution of a viral gene is impossible in the absence of the LTRs. This strategy is appropriate for "simple" viruses having few reading frames. In other versions, each of the proteins necessary may be placed in an independent expression cassette. For complex viruses such as HIV, several cassettes may be in succession (gag/pol, env, tat, rev, nef).

Another example of a plasmovirus according to the invention is represented in FIG. 2 and may comprise:

a) the env gene of a retrovirus under the control of a specific promoter, b) a defective retroviral genome comprising the LTR sequences, the gag and pol genes and, where appropriate, the Psi sequence, c) where appropriate, a gene or gene fragment of interest whose expression depends either on the promoter in a) or the promoter in b), d) where appropriate, the Us11 gene from HSV.

This construct, similar to that of the plasmoviruses already described in the state of the art, allows the expression, by the transduced cell, of a foreign gene which may be for example a gene encoding an immunostimulant protein. Furthermore, in a $\psi$+ version of this construct, infectious but defective particles are produced. Thus, cells may be infected and may again express the proteins necessary for the formation of viral particles. If these cells are antigen-presenting cells, this may be particularly advantageous.

Another embodiment of a vector according to the invention may comprise:

a) the gag, pol and/or env genes of a retrovirus under the control of a specific promoter, b) a defective retroviral genome comprising the LTR sequences and the Psi sequence, c) where appropriate, a gene or gene fragment of interest whose expression depends either on the promoter in a) or the promoter in b), d) where appropriate, the Us11 gene from HSV.

Another example of a plasmovirus is represented in FIG. 3 and comprises an attenuated viral genome lacking the $\psi$ sequence and in which several rearrangements are introduced into the genome in order to avoid the appearance of replicating viruses. The 3' LTR is replaced with a different polyadenylation site; mutations (point mutations, deletions, change in reading frame and the like) are made in one or more non-structural proteins (reverse transcriptase RT, integrase IN). This strategy is particularly appropriate for complex genomes such as HIV which possess a large number of proteins. Their synthesis, which is complex, thus remains under the homologous control of the HIV 5' LTR.

For all the constructs (FIGS. 1, 2, 3), one or more expression cassettes encoding genes promoting an immune response can be added to the plasmid. Furthermore, the elements promoting the expression of the plasmid may also be added: AAV ITR, sequences which can promote the replication of the plasmid (SV40 or EBV replication origin and T antigen or ebna expression cassette for example), and the like.

The present invention also relates to an immunogenic composition, especially a vaccine, for the prophylaxis and/or therapy of individuals infected or capable of being infected with a virus, and containing at least one plasmovirus as defined above.

The relevant subjects are humans and animals, and the immunogenic compositions or vaccines may belong to human or veterinary medicine.

This composition is immunogenic more particularly in the sense that the injection of the vector carrying the defective viral genome allows the reconstitution of a physical particle capable of eliciting a cellular and/or humoral immune response.

The defective viral genome and the sequences encoding the gene(s) allowing the reconstitution of the viral envelope may be carried by one or two vectors, which are combined in the composition, these may be linked by means known to a person skilled in the art, especially those described in patent application WO 95/26411. In this case, the term plasmovirus applies at the same time to a single vector carrying at the same time the sequences specific for the defective viral genome, and the sequences encoding the structural protein(s) as well as, where appropriate, the sequences encoding the exogenous genes cited above, either for increasing the immunogenic power, or for increasing the safety of the system, or finally for allowing better expression of the proteins of the viral envelope.

The immunogenic composition may also contain, as an active ingredient, cells which have been previously transfected in vitro with a plasmovirus or a vector as described above. In this case, an injection of the composition allows grafting of the host cell in vivo and the reconstitution of a viral particle which is then capable of triggering the desired immune response.

The immunogenic composition may where appropriate contain, combined with the plasmovirus, a vaccination adjuvant. The adjuvants may be of several types; some promote the conventional immune response such as an adjuvant of the N-acetyl-muramyl type combined with a peptide such as MDP or its various derivatives such as those described in CRS Critical Reviews in Immunology, 1988, Vol. 8, pages 83–100. Other types of adjuvant may be envisaged, such as those which promote the penetration of the nucleic acid sequences into the cells. Finally, the plasmovirus in the immunogenic composition may be linked to a sequence known to be or presumed to be T-dependent or, alternatively, linked or enclosed in liposomes. It may also be administered in aqueous or an oily media, in the form of subcutaneous, intramuscular or intravenous injections by means of "pellets" (biodegradable polymers containing the product) and/ or implantation of the system of release by a micropump. Other adjuvants, such as PAO, alone or combined with lecithin (EP445-710) ZN(OH) or HBW538 (Drugs experimental clinical research (1991) 17 (9): 445450) combined with aluminium hydroxide $(Al(OH)_3)$, covalently or otherwise, with the active ingredient for the composition. The immunogenic composition in which one of the active ingredients is the plasmovirus is also characterized in that the defective viral genome carries a suicide gene so as to allow the safety of the system by adding, where appropriate, ganciclovir when it is desired to stop the proliferation of the virus.

In the immunogenic composition of the invention, the plasmovirus may be either naked or coated DNA, or naked DNA combined with a cell of the packaging cell type or a cell established as a line which may be chosen, for example, from the fibroblast lines such as the 3T3 line or lines capable of being cultured in suspension such as myeloma cells, Vero cells or MRC5 cells. In this case, the immunogenic composition is the combination of the plasmovirus and of the host cell which acts, in this particular case, as a cellular graft allowing production of the viral particle which will itself allow eliciting of the vaccinal reaction.

The immunogenic composition of the invention is characterized in that it contains from 0.1 to 1000 $\mu$g of nucleic acids constituting the said vector per dose and preferably from 10 to 500 $\mu$g per dose. These doses are understood to be a unit dose intended for humans.

In the immunogenic composition of the invention, the plasmovirus may also be a virus such as the adenovirus or the AAV (adeno-associated virus) which is defective and carries all the sequences necessary for the reconstitution of a retrovirion; in other words, the defective virus, carrying the retroviral sequences, plays the role of carrier in relation to cells which should be preferably targeted.

By way of example, the AAV has a particular tropism for the muscle cells which have a strong immunogenic capacity; the introduction of the genome carrying the retroviral sequences into this type of cells may increase the vaccinating effect thereof.

In this embodiment, the plasmovirus composition contains from 100 to $10^6$ defective viral particles per unit dose intended preferably for humans.

The present invention also relates to a method of active immunization of the individual against a viral infection, the said method consisting in injecting into an individual a plasmovirus carrying the structural genes necessary for the reconstitution of a viral particle.

The injected plasmovirus may carry, in addition, a viral or retroviral genome, preferably defective and carrying non-coding and/or regulatory sequences of the virus or of the retrovirus, and where appropriate an encapsidation sequence. The retroviral genomes which are preferred in the context of a vaccination method are those of the lentiviruses, the oncornaviruses, the spumaviruses or the type D retroviruses. In this case as well, the structural genes necessary for the constitution of the viral particle are preferably the genes encoding gag and/or env. The env gene is chosen according to the aim assigned to the plasmovirus, various examples being cited above. The env gene may be recombined such that a chimera is produced which carries both the function for attachment to the receptor of the target cells of the virion and of the receptor of the insert in the env molecule. As stated above, it may also be advantageous to add the HSV1 Us11 gene to the plasmovirus so as to stimulate the synthesis of the structural proteins.

The various embodiments of the vectors used in the vaccination have been described above.

The method of vaccination may also consist in treating the individual infected or capable of being infected with a host cell previously transfected with the vectors of the invention and in particular the type 3T3 fibroblast lines or the lines cultured in suspension such as the myeloma cells or the Vero cells.

When the retroviral genome lacks the encapsidation sequence, the physical particles reconstituted then lack a genome. In contrast, when the viral genome carries this encapsidation sequence, it may be advantageous to construct the vector such that under the control of the retroviral promoter, a gene of interest is added so as to increase the safety of the system or to increase the immune response of the vaccine.

This immunization may be obtained after percutaneous or subcutaneous, intramuscular or intravenous injection of an immunogenic composition as described above. These plasmoviruses may also be used in the manufacture of the immunogenic composition and in particular of a vaccine so as to prevent or treat viral infections, this use forming part of the invention.

The use of plasmoviruses is advantageous since the preparation and the preservation of nucleic acids is easier to carry out than the production and preservation of complete viral particles.

The formation of defective viral particles may be induced either in vitro in cells in culture, or in vivo after intramuscular, intravenous or subcutaneous injection of the immunogenic composition, or ex vivo after injection of the transformed cells.

Finally, the process for the manufacture of a live vaccine consisting of a reconstituted, preferably defective, viral particle forms part of the invention; it comprises the transfection of cells with a vector as described above, comprising, on the one hand, the structural gene necessary for the reconstitution of the viral particle and, on the other hand, the defective retroviral genome, the structural genes of the virus being either under the control of a specific promoter, or under the control of a viral promoter.

The transfected cells in the process of the invention are either cells in culture and the transformation is carried out in vitro, or the cells are those of an individual and are transfected in vivo or ex vivo.

This process is particularly advantageous from the economic point of view, on the one hand, and from the safety point of view on the other. Indeed, the production of plasmoviruses is simple, and the stability and reproducibility more consistent with the constraints of drug production. Moreover, this makes it possible to avoid the handling of viral particles which, at one stage of a process for the preparation, for example, of live vaccines using attenuated or inactivated whole viruses, could be dangerous.

Persons skilled in the art will know how to use on a case-by-case basis the techniques which are most appropriate for the transfection of one cell type or another. The examples below, as well as the diagrams whose legends follow, serve to illustrate the invention without limiting its scope.

The example below and the comparative example show the efficiency of the vaccinal approach on an animal model.

In this example, FIG. 4 represents the plasmid pBMC-3 comprising an HSV1-TK gene under the control of an Mo-MuLV 5' LTR promoter.

FIG. 5 represents the plasmid pNP-2.

FIG. 6 represents the variation in the weight of the animals vaccinated with the aid of these constructs and infected with the murine myeloproliferative leukaemia virus. The days of the examination are indicated on the x-axis and the variations in the weight of the animals on the y-axis.

I. Experimental model used:

The experimental model used is the induction of a megakaryocytic leukaemia in mice. This leukaemia is induced by infecting mice with a pathogenic retrovirus of the MPLV type. The MPLV virus is derived from the murine leukaemia viruses of the Friend type. The latter have LTR sequences distinct from the Moloney-type viruses but have extremely similar structural protein sequences. It is therefore possible to vaccinate against MPLV using proteins derived from the Moloney viruses.

Such a virus carries a v-mpl oncogene, which is the ligand for thrompoietin. After infection with such a virus, the mouse develops megakaryotic leukaemia within a few weeks. This disease is characterized by a splenomegaly and a hepatomegaly; more precisely, after viral infection, an extremely large number of lymphocytes accumulate in the spleen. Accordingly, a vaccinating effect may be assessed by the absence of an increase in the weight of the spleen, of the liver or of the whole animal after a challenge with the pathogenic virus.

Figure 1:
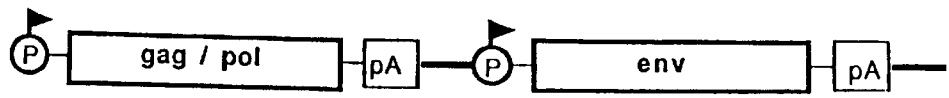
FIG. 1 represents an example of a plasmovirus construct.
Figure 2:
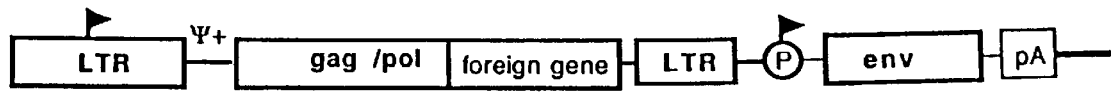
FIG. 2 represents a plasmovirus according to the invention.
Figure 3:
FIG. 3 represents an example of a plasmovirus.
Figure 4:
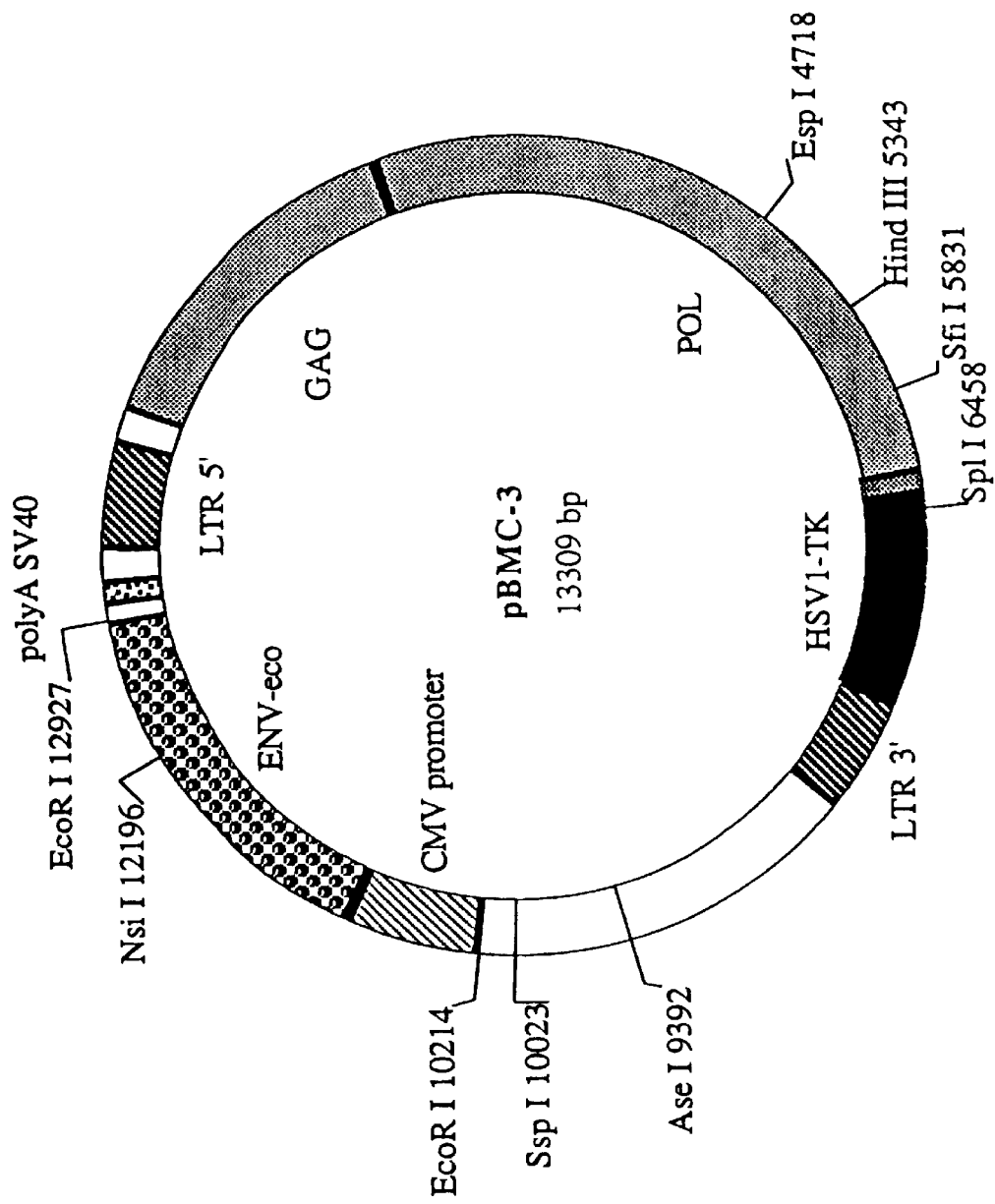
FIG. 4 represents the plasmid pBMC-3.
Figure 5:
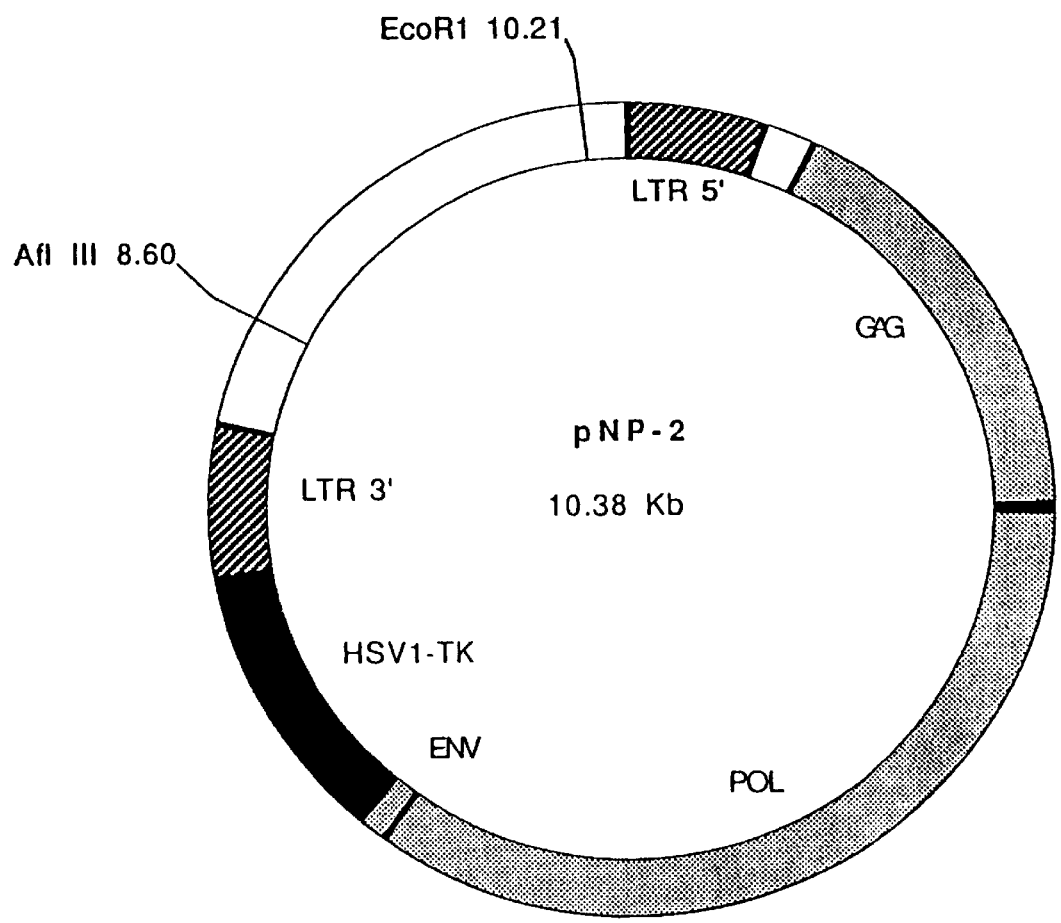
FIG. 5 represents plasmid pNP-2.

II. Plasmoviruses used in this model:

The vaccination was carried out with three different plasmoviruses which are the following:

The plasmid pNP-2, represented in FIG. 5, is a plasmid of 10,380 base pairs. In this plasmid, the first ATG codon of the env gene of a provirus derived from Moloney has undergone a point mutation so as to retain the direction of the corresponding codon in the pol gene which is superposed. A few base pairs downstream of the stop codon of the pol gene, an HSV1-TK gene was inserted so as to remove any sequence from the env gene between the stop codon of this transgene and the polypurine fraction of the LTR in 3'. In such a construct, the gag and pol genes are obtained from an uncut genomic RNA whereas the transgene is transcribed from a spliced RNA using donor and acceptor splicing sites of the wild-type provirus. A cassette for expression of the env gene was then constructed so as to reduce the possibility of recombination leading to infectious viruses;

pBMC-3, represented in FIG. 4, is the same as the plasmid pNP-2 but comprises, in addition, the ecotropic env gene;

The plasmid pBPXT4 incorporating the human gene for CD4 and lacking the env gene, not represented here, was used as control.

III. Protective prophylactic effect of the plasmoviruses in the animal model:

Adult mice are injected intramuscularly as described by Ulmer et al., Science, 1993 259: 1745–1749.

The injections at the rate of 100 µg of plasmid prepared by Qiagen per mouse are repeated three times at an interval of one week.

As a group for controlling the efficacy of the vaccination, the mice are injected with plasmid DNA completely foreign to the MPLV virus.

At the end of the immunization procedure, the animals are injected intravenously with a supernatant from the culture of a cell line producing the MPLV virus.

This undiluted supernatant has a reverse transcriptase (RT) activity of 66,152 $CPM/10^6$ cells. This supernatant was diluted 100-fold and 200 microlitres were injected into the mice intravenously and the time of injection corresponds to the time 0 on the curve in FIG. 6.

Four groups of animals were treated; each group consisted of five ten-week old dBA/2 mice at the beginning of the experiment, that is to say at the first vaccination.

At various times after the injection of the MPLV particles, the animals are weighed when they are still alive and/or sacrificed and the weight of the spleen and of the liver weighed respectively. The times for the measurement and for the removal of the sample are taken at 7, 14, 21, 28 and 35 days.

Figure 6:
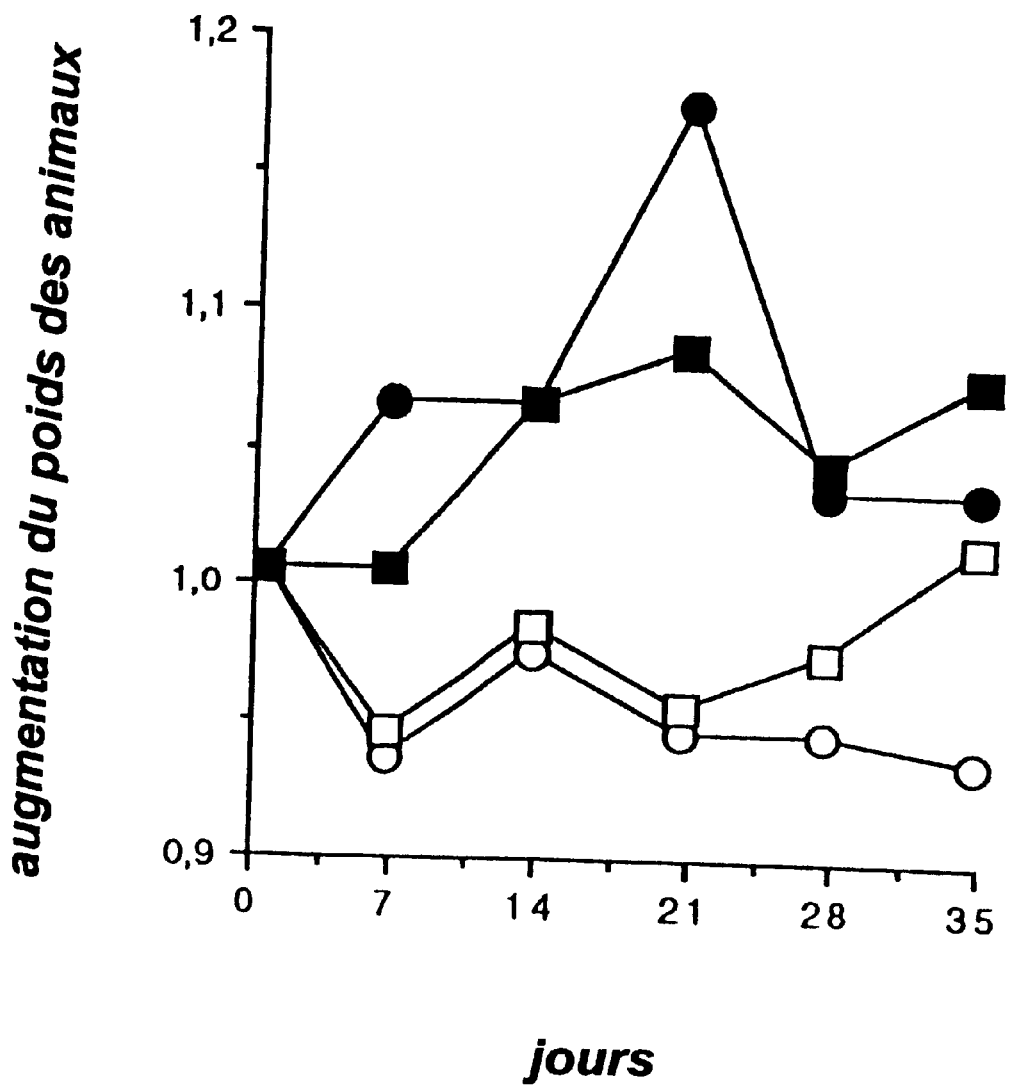
FIG. 6 represents the variation in the weight of the animals vaccinated with the aid of the disclosed constructs and infected with the murine myeloproliferative leukemia virus.

IV. Results:

FIG. 6 represents the variation in the weight of the animal at various times after the challenge with the MPLV particles. The white rings represent the results obtained after vaccination with the plasmid pBMC-3. The black ring represents the results obtained after vaccination with pNP-2. The white square represents the results obtained with pBXT4, the plasmid providing the cDNA for the human CD4, and the black squares represent the control in which the mice were not vaccinated prior to the injection of the viral particles.

The table below indicates respectively the weight of the spleen and of the liver after removal, 21 days after the injection of the viral particles.

| Type of vaccination | Increase in the weight of the spleen at the 21st day | Increase in the weight of the liver at the 21st day |
| --- | --- | --- |
| pBMC-3 | × 1 | × 0.8 |
| pNP-2 | × 16.3 | × 1.3 |
| hCD4 | × 12.5 | × 1.3 |
| no vaccine | × 11.0 | × 1.1 |

Conclusion:

The results show clearly that the vaccination with pBMC-3 is effective since no increase in weight was observed either in the mouse or in the spleen or in the liver. By contrast, the use of the other three plasmoviruses leads to an increase of at least 10-fold in the weight of the spleen, indicating the development of the disease and inefficiency of the vaccination. This result shows clearly that the plasmovirus integrated into a composition gives rise to an active agent capable of preventing the pathogenic effect of a viral infection.

What is claimed is:

1. A vaccine comprising a vector wherein said vector comprises:
   (a) a gag gene and a pol gene of a retrovirus under the control of a first promoter wherein said first promoter is different from the promoter of said retrovirus;
   (b) a first polyadenylation signal which is different from the long terminal repeat of said retrovirus and is 3' from said gag gene and pol gene;
   (c) an env gene of a retrovirus under the control of a second promoter wherein said second promoter is different from the promoter of said retrovirus; and
   (d) a second polyadenylation signal which is different from the long terminal repeat of said retrovirus; and is 3' from said env gene.

2. The vaccine according to claim 1, wherein said vector further comprises a ψ sequence.

3. The vaccine according to claim 1, wherein said vector further comprises a gene or a gene fragment encoding a peptide, a polypeptide or a protein and is inserted into a N-terminal part of the env gene.

4. The vaccine according to claim 1, wherein said first promoter and said second promoter is selected from the group of a CMV promoter, a SV40 promoter, a PGK promoter and a TK promoter.

5. The vaccine according to claim 1, wherein said first and second polyadenylation signals are selected from the group of a SV40 polyadenylation signal, a TK polyadenylation signals and an HBV polyadenylation signal.

6. A method of inducing an immune response in a mammal comprising administering the vaccine of claim 1 to said mammal.

7. A vaccine comprising:
   a vector wherein said vector comprises:
   (a) a defective retroviral genome comprising the long terminal repeat sequences, a gag gene and a pol gene of a retrovirus;
   (b) an env gene of a retrovirus under the control of:
      (i) a promoter wherein said promoter is different from the promoter of said virus; and
      (ii) a polyadenylation signal which is different from the long terminal repeat of said virus and is 3' from said env gene.

8. The vaccine according to claim 7, wherein said vector comprising said defective viral genome further comprises a ψ sequence which is 5' from said gag gene and said pol gene.

9. The vaccine according to claim 7, wherein said vector further comprises a gene or a gene fragment encoding a peptide, a polypeptide or a protein.

10. The vaccine according to claim 9, wherein said gene or said gene fragment is on an independent expression cassette.

11. The vaccine according to claim 7, wherein said promoter is selected from the group of a CMV promoter, a SV40 promoter, a PGK promoter and a TK promoter.

12. The vaccine according to claim 7, wherein said polyadenylation signal is selected from the group of a SV40 polyadenylation signal, a TK polyadenylation signals and an HBV polyadenylation signal.

13. The vaccine according to claim 7, wherein said vector further comprises a Us11 gene from HSV.

14. A vaccine comprising:
   a vector wherein said vector comprises:
   (a) an attenuated retroviral genome lacking a ψ sequence comprising:
      (i) a 5' long terminal repeat sequence;
      (ii) a gag gene;
      (iii) a mutated reverse transcriptase or an integrase gene;
      (iv) an env gene; and
      (v) a polyadenylation signal which is different from the long terminal repeat of said virus and is 3' from said env gene.

15. The vaccine according to claim 14, wherein said vector comprising said attenuated retroviral genome is an attenuated HIV genome.

16. The vaccine according to claim 14, wherein said polyadenylation signal is selected from the group of a SV40 polyadenylation signal, a TK polyadenylation signals and an HBV polyadenylation signal.

17. A vaccinal vector comprising:
   (a) a defective retroviral genome comprising long terminal repeat sequences, a gag gene and a pol gene of a retrovirus and lacking a Psi sequence;

(b) an env gene of a retrovirus under the control of a promoter wherein said promoter is different from the promoter of said virus; and (c) a polyadenylation signal which is different from the long terminal repeat of said retrovirus and is 3' from said env gene.

18. The vector according to claim 17, wherein said vector further comprises a gene or a gene fragment encoding a peptide, a polypeptide or a protein and is inserted 5' from said gag gene and said pol gene.

19. The vector according to claim 18, wherein said gene is a thymidine kinase from HSV1-TK.

20. The vector according to claim 18, wherein said gene is a cytokine or a MHC or a B7 protein.

21. The vector according to claim 17, wherein said vector further comprises a Us11 gene from HSV.

22. An immunogenic composition comprising the vector according to claim 17.

23. The immunogenic composition according to claim 22, wherein said retrovirus in said vector is an HIV or an HTLV or a spumavirus or a type D retrovirus.

24. A process for manufacturing a live vaccine said process comprising the step of:

(a) transfecting cells in vivo or ex vivo with a vector according to claim 17.

* * * * *